US011447812B2

(12) United States Patent
Pierechod et al.

(10) Patent No.: US 11,447,812 B2
(45) Date of Patent: Sep. 20, 2022

(54) SINGLE-STRAND BINDING PROTEIN

(71) Applicant: Universitetet I Tromsø—Norges Arktiske Universitet, Tromsø (NO)

(72) Inventors: Marcin Pierechod, Kvaløysletta (NO); Nils Peder Willassen, Tomasjord (NO); Ulli Rothweiler, Tomasjord (NO)

(73) Assignee: UNIVERSITETET I TROMSØ—NORGES ARKTISKE UNIVERSITET, Tromsø (NO)

( * ) Notice: Subject to any disclaimer, the term of this patent is extended or adjusted under 35 U.S.C. 154(b) by 318 days.

(21) Appl. No.: 16/488,477

(22) PCT Filed: Feb. 23, 2018

(86) PCT No.: PCT/EP2018/054593
§ 371 (c)(1),
(2) Date: Aug. 23, 2019

(87) PCT Pub. No.: WO2018/154083
PCT Pub. Date: Aug. 30, 2018

(65) Prior Publication Data
US 2019/0376122 A1     Dec. 12, 2019

(30) Foreign Application Priority Data

Feb. 24, 2017 (GB) ..................................... 1703049

(51) Int. Cl.
*C12Q 1/6806* (2018.01)
*C07K 14/195* (2006.01)

(52) U.S. Cl.
CPC .......... *C12Q 1/6806* (2013.01); *C07K 14/195* (2013.01); *C12Q 2522/101* (2013.01); *C12Q 2525/117* (2013.01); *C12Q 2527/125* (2013.01); *C12Q 2527/137* (2013.01)

(58) Field of Classification Search
CPC ............ C12Q 1/6806; C12Q 2522/101; C12Q 2527/125; C12Q 2527/137; C12Q 1/6832; C07K 14/195
See application file for complete search history.

(56) References Cited

U.S. PATENT DOCUMENTS

2016/0257942 A1    9/2016 Bruce et al.

FOREIGN PATENT DOCUMENTS

| JP | 2010263845 A | 11/2010 |
|----|--------------|---------|
| JP | 2012231799 A | 11/2012 |
| WO | 9106679 A1 | 5/1991 |
| WO | 2008062777 A1 | 5/2008 |
| WO | 2017013400 A1 | 1/2017 |

OTHER PUBLICATIONS

Proc. Natl. Acad. Sci. U.S.A. 102:18147-18152 (Year: 2005).*

International Search Report and Written Opinion issued in International Application No. PCT/EP2018/054593, dated May 29, 2018, 17 pages.
Combined Search and Examination Report issued in Great Britain Application No. GB1703049.5, dated Dec. 20, 2017, 9 pages.
Mongodin et al., "The genome of Salinibacter ruber: Convergenceand gene exchange among hyperhalophilic bacteria and archaea", GENBANK accession No. ABC44897.1, PNAS, vol. 102, No. 50, Dec. 2005, pp. 18147-18152.
Gourves et al., "Equilibrium Binding of Single-stranded DNA with Herpes Simplex Virus Type I-coded Single-stranded DNA-binding Protein, ICP8", J of Biol Chem, vol. 275, No. 15, Apr. 2000, pp. 10864-10869.
Palanichelvam et al., "The capsid protein of tomato yellow leaf curl virus binds cooperatively to single-stranded DNA", J of General Virology, vol. 79,1998, pp. 2829-2833.
Anton et al., "Distribution, abundance and diversity of the extremely halophilic bacterium Salinibacter ruber", BioMed Central, Oct. 28, 2008, pp. 1-10.
Makhdoumi-Kakhki, et al. "*Salinibacter iranicus* sp. nov. and *Salinibacter luteus* sp. nov., isolated from a salt lake, and emended descriptions of the genus *Salinibacter* and of *Salinibacter ruber*", International Journal of Systematic and Evolutionary Microbiology (2012), 62, pp. 1521-1527.
K. Hatch, et al., "Measurement of the salt-dependent stabilization of partially open DNA by *Escherichia coli* SSB protein", Nucleic Acids Research, 2008, vol. 36, No. 1, Nov. 21, 2007, pp. 294-299.
Nicholas P. George, et al., "Structure and Cellular Dynamics of Deinococcus radiodurans Single-stranded DNA (ssDNA)-binding Protein (SSB)-DNA Complexes*s", The Journal of Biological Chemistry vol. 287, No. 26, Jun. 22, 2012, pp. 22123-22132.
Ma, et al., "Meeting Review", Halophiles 2010: Life in Saline Environments, Applied and Environmental Microbiology, vol. 76, No. 21, Nov. 2010, pp. 6971-6981.
Aharon Oren "Salinibacter: an extremely halophilic bacterium with archaeal properties", Minireview, Department of Plant and Environmental Sciences, The Alexander Silberman Institute of Life Sciences, The Hebrew University of Jerusalem, Israel, FEMS Microbiol Lett 342 (2013), pp. 1-9.

(Continued)

*Primary Examiner* — Cynthia B Wilder
(74) *Attorney, Agent, or Firm* — Rothwell, Figg, Ernst & Manbeck, P.C.

(57) ABSTRACT

The present invention relates to the use of a single-strand DNA binding protein (SSB) which exhibits at least 50% of its maximum ssDNA binding capability in the presence of 500 mM of sodium ions, to dehybridize a DNA molecule or to prevent hybridisation of a complementary ssDNA, wherein the SSB comprises the amino acid sequence of SEQ ID NO:1 or an amino acid sequence which is at least 75% identical to SEQ ID NO:1, or a functional fragment thereof, and wherein the DNA molecule or ssDNA is present in or exposed to a solution containing one or more of the following (i) at least 350 mM of sodium ions; (ii) at least 50 mM of potassium ions; (iii) at least 150 mM of magnesium ions; or (iv) at least 200 mM of calcium ions.

11 Claims, 5 Drawing Sheets

Figure 1:
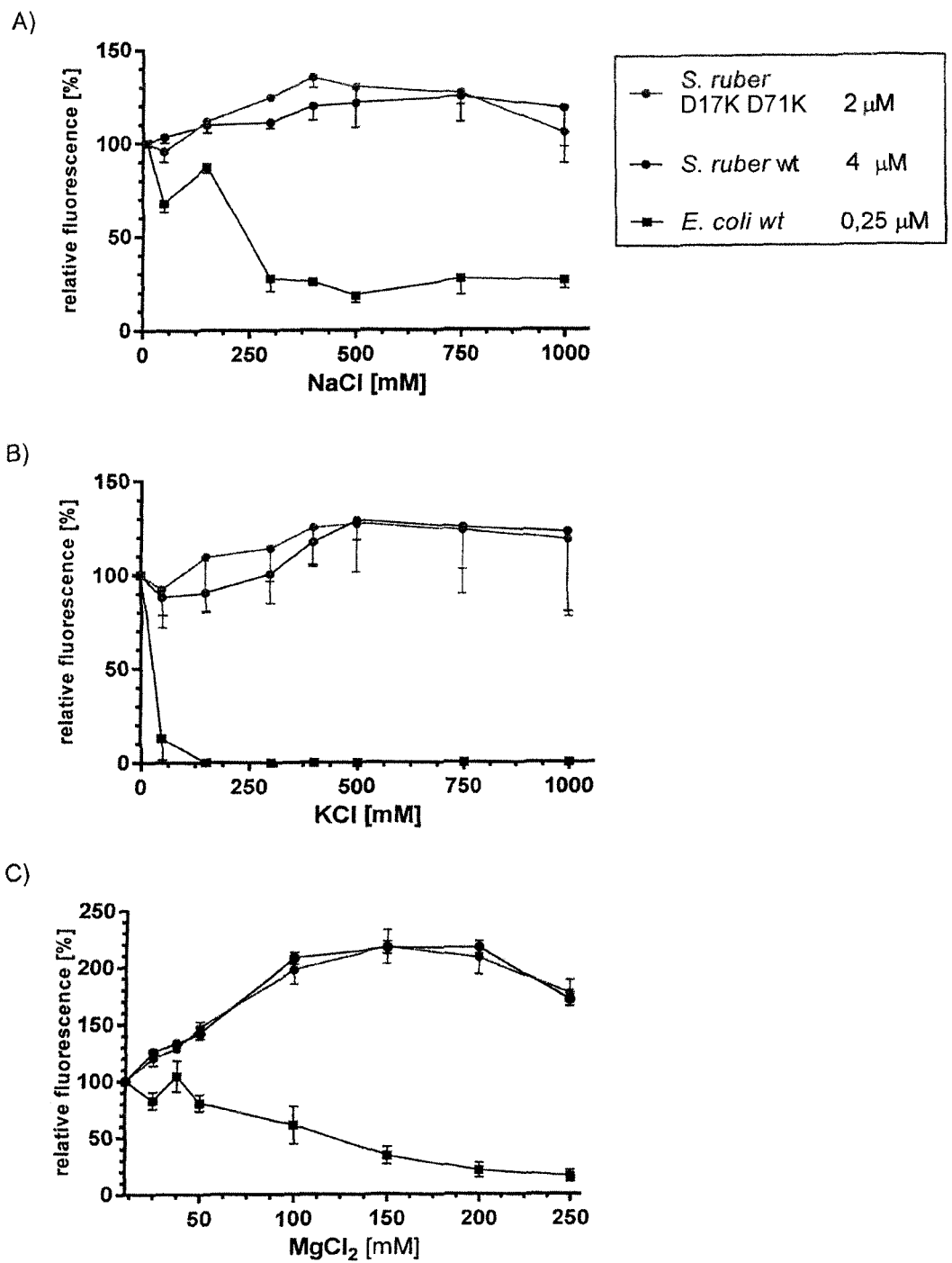
Figure 1:
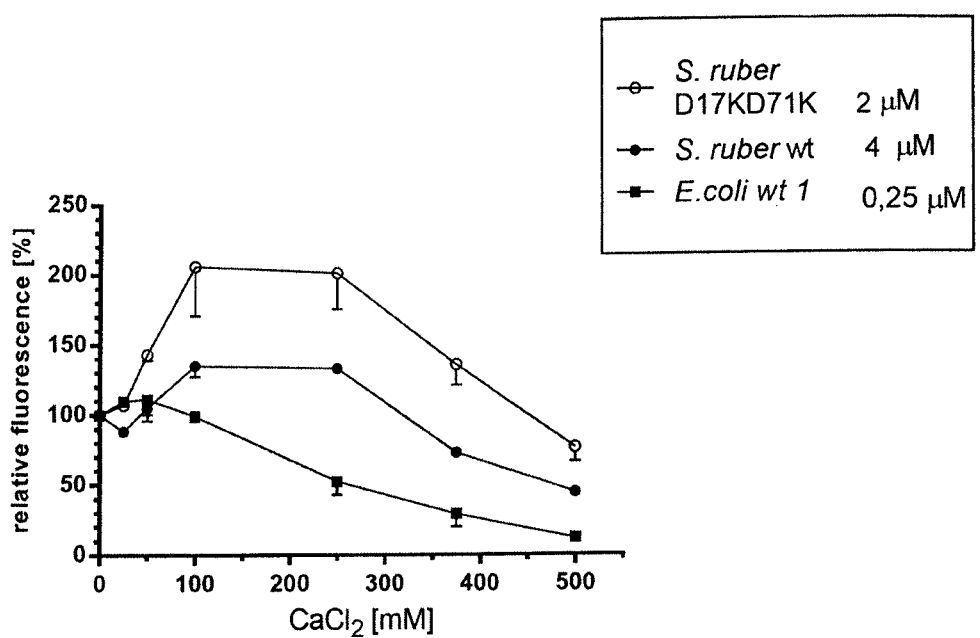

Specification includes a Sequence Listing.

(56) References Cited

OTHER PUBLICATIONS

Perales, et al., "Enhancement of DNA, cDNA synthesis and fidelity at high temperatures by a dimeric single-stranded DNA-binding protein", Nucleic Acids Research, vol. 31, No. 22, 2003, pp. 6473-6480.

Shi et al., "Systematic Functional Comparative Analysis of Four Single-Stranded DNA-Binding Proteins and Their Affection on Viral RNA Metabolism", PLOS One, vol. 8, Issue 1, Jan. 2013, pp. 1-11.

Chrysogelos, et al., "*Escherichia coli* single-strand binding protein organizes singlestranded DNA in nucleosome-like units", Biochemistry, Proc. NatL Acad. Sci. USA, vol. 79, Oct. 1982, pp. 5803-5807.

Kilianski, et al., "Use of Unamplified RNA/cDNA-Hybrid Nanopore Sequencing for Rapid Detection and Characterization of RNA Viruses", Emerging Infectious Diseases, vol. 22, No. 8, Aug. 2016, pp. 1448-1451.

David E. Draper, "A guide to ions and RNA structure", Department of Chemistry, Johns Hopkins University, RNA, vol. 10, No. 3, (2004), pp. 10:335-10:343.

Tang et al., "Fluorescence turn-on detection of a protein through the displaced single-stranded DNA binding protein binding to a molecular beacon", Chem. Commun., 2011, 47, pp. 5485-5487.

Overman et al., Equilibrium Binding of *Escherichia coli* Single-Strand Binding Protein to Single-Stranded Nucleic Acids in the (SSB)65 Binding Mode. Cation and Anion Effects and Polynucleotide Specificity, Biochemistry 1988, 27, pp. 456-471.

Mostafa Ronaghi, "Improved Performance of Pyrosequencing Using Single-Stranded DNA-Binding Protein" Analytical Biochemistry 286, Jul. 5, 2000, pp. 282-288.

Ducani et al. "Rolling circle replication requires single-stranded DNA binding protein to avoid termination and production of double-stranded DNA" Nucleic Acids Research, 2014, vol. 42, No. 16, pp. 10596-10604.

* cited by examiner

A

B

A

B

SINGLE-STRAND BINDING PROTEIN

CROSS-REFERENCE TO RELATED APPLICATIONS

The present application is a national stage filing under 35 U.S.C. § 371 of PCT/EP2018/054593, filed on 23 Feb. 2018, which in turn claims the benefit of priority to and the benefit of GB Application No. 1703049.5, filed 24 Feb. 2017. Each application is incorporated herein by reference in its entirety.

The present invention relates to single-strand (also known as single-stranded) DNA-binding proteins (SSB), in particular to a class of SSB, which is able to function at high salt concentrations.

Single-strand DNA-binding proteins (SSB) are able to bind single-strand DNA (ssDNA) and RNA, forming a nucleoprotein complex, while their affinity for double-stranded DNA is low. The nucleic acid present in such complexes can then serve as a substrate for polymerases or other DNA or RNA modifying enzymes. The best characterized SSB is from *E. coli*, a 178 amino acid protein which binds ssDNA as a homotetramer.

SSB is involved in DNA replication and recombination in vivo, effectively maintaining separation (preventing reannealing) of the unzipped DNA duplex and keeping the two strands in single-strand form. SSB can be used in all applications where DNA or RNA needs to be preserved in single-strand form. Polymerase chain reaction (PCR) technology can be optimised by adding SSB, which can stabilize denatured DNA, preventing duplex formation and protecting ssDNA from digestion by nucleases. SSB is also used in Reverse Transcription PCR and isothermal amplification of nucleic acid. Other applications include use in combination with RecA in site-directed mutagenesis. SSB stimulates specific DNA polymerases used in DNA sequencing reactions and in the context of Pyrosequencing technology it—increases signal intensity, decreases nonspecific signals and improves polymerization efficiency.

The utility of SSB in molecular biology is clear, however, the proficiency of SSB is heavily dependent on the type and concentration of salt present in the reaction mixture (Nucleic Acid Research [2008] Vol. 36 No. 1 p 294-9). In particular, there is no commercially available SSB which is able to form a stable nucleoprotein complex at elevated salt concentrations. Salt-stable nucleoprotein complexes would be able to withstand washing with high-salt buffers, which is highly desirable, for example in "next-generation" DNA sequencing, e.g. the Illumina workflow methods. A need has been identified for a SSB that can form a stable nucleoprotein complex in a broad range of salt conditions, in particular at elevated salt concentrations, and for methods of nucleic acid amplification and sequencing which can be performed in the presence of a high concentration of salt.

The present inventors have developed such methods employing suitably compatible SSB molecules.

In a first aspect the present invention provides a method of nucleic acid amplification or sequencing wherein the reaction mixture or sample solution contains a single-strand DNA binding protein (SSB) which exhibits at least 50% of its maximum ssDNA binding capability in the presence of 500 mM of sodium ions.

In a further aspect, the present invention provides a method of site directed mutagenesis wherein the reaction mixture contains a single-strand DNA binding protein (SSB) which exhibits at least 50% of its maximum ssDNA binding capability in the presence of 500 mM of sodium ions.

In a further aspect, the present invention provides a method of examining (e.g. intracellular) nucleic acid structures in a sample using a microscope, wherein the nucleic acid sample is contacted with a single-strand DNA binding protein (SSB) which exhibits at least 50% of its maximum ssDNA binding capability in the presence of 500 mM of sodium ions. In such methods the SSB stabilizes and/or marks regions of ssDNA.

In such methods, for example, an electron microscope or fluorescence microscope may be used. The SSB employed in a method of fluorescence microscopy may be a fluorescent derivative, e.g. incorporating a fluorescent label.

In a further aspect, the present invention provides a method of restriction enzyme digestion wherein the reaction mixture contains a single-strand DNA binding protein (SSB) which exhibits at least 50% of its maximum ssDNA binding capability in the presence of 500 mM of sodium ions.

In a further aspect, the present invention provides a method of reverse transcription (e.g. as a first step in a method of RT-PCR), wherein the reaction mixture contains a single-strand DNA binding protein (SSB) which exhibits at least 50% of its maximum ssDNA binding capability in the presence of 500 mM of sodium ions.

In a further aspect, the present invention provides a method of enhancing the activity of T4 polymerase, which method comprises contacting said T4 polymerase with a single-strand DNA binding protein (SSB) which exhibits at least 50% of its maximum ssDNA binding capability in the presence of 500 mM of sodium ions. Alternatively viewed, the invention provides the use of a single-strand DNA binding protein (SSB) which exhibits at least 50% of its maximum ssDNA binding capability in the presence of 500 mM of sodium ions to enhance the activity of T4 polymerase.

The target nucleic acid for SSB binding in the above methods is preferably ssDNA but may be RNA.

In a further aspect, the present invention provides a method of protecting ssDNA or RNA from nuclease digestion wherein the reaction mixture contains a single-strand DNA binding protein (SSB) which exhibits at least 50% of its maximum ssDNA binding capability in the presence of 500 mM of sodium ions. Such protection may be of use in methods of sample/product "clean-up" or purification. Alternatively viewed, the invention provides the use of a single-strand DNA binding protein (SSB) which exhibits at least 50% of its maximum ssDNA binding capability in the presence of 500 mM of sodium ions to protect ssDNA from nuclease digestion. Alternatively viewed the invention provides a method of protecting ssDNA or RNA from nuclease digestion, which method comprises contacting said ssDNA or RNA with a single-strand DNA binding protein (SSB) which exhibits at least 50% of its maximum ssDNA binding capability in the presence of 500 mM of sodium ions.

In a further aspect, the present invention provides a method of nucleic acid purification, i.e. isolating one or more nucleic acid molecules from a sample, wherein the sample is contacted with a single-strand DNA binding protein (SSB) which exhibits at least 50% of its maximum ssDNA binding capability in the presence of 500 mM of sodium ions. Preferably, the nucleic acid molecule is a DNA molecule, preferably of size ≥0.5 Mbp, more preferably ≥1 Mbp. Due to their size, such large DNA fragments are prone to mechanical breakage during isolation. However, the use of the SSB of the present invention stabilizes the DNA structure permitting isolation of intact molecules.

In each case, the method or use described above employs a SSB which exhibits at least 50% of its maximum ssDNA binding capability in the presence of 500 mM of sodium ions; such a property means that the SSB is tolerant of and active at high salt concentrations, i.e. can be considered halophilic.

Methods of nucleic acid sequencing, amplification, mutagenesis, examination, digestion and reverse transcription as described above are well known in the art and standard conditions and reagents may be employed.

Many of the methods of the invention defined above involve nucleotide polymerisation using a DNA polymerase. Typically said method comprises providing a reaction mixture comprising a DNA polymerase, a template nucleic acid molecule, an SSB which exhibits at least 50% of its maximum ssDNA binding capability in the presence of 500 mM of sodium ions, an oligonucleotide primer which is capable of annealing to a portion of the template nucleic acid molecule and one or more species of nucleotide (e.g. deoxynucleoside triphosphates, dNTPS) and incubating said reaction mixture under conditions whereby the oligonucleotide primer anneals to the template nucleic acid molecule and said DNA polymerase extends said oligonucleotide primer by polymerising one or more nucleotides. Suitable conditions are well known in the art. Optionally, the generation of the polynucleotide product is detected (e.g. via gel electrophoresis).

A single-strand DNA binding protein (SSB) which exhibits at least 50% of its maximum ssDNA binding capability in the presence of 500 mM of sodium ions may be referred to herein as an SSB of the invention. It may be used in conventional methods where standard commercially available SSB may be used, e.g. *E. coli* SSB, but advantageously it is used in methods employing high salt concentrations.

The above methods and uses (e.g. amplification, sequencing and site directed mutagenesis) will typically employ a reaction mixture, sample solution or washing buffer containing one or more of the following:
   (i) at least 350 mM of sodium ions,
   (ii) at least 50 mM of potassium ions,
   (iii) at least 150 mM of magnesium ions, or
   (iv) at least 200 mM of calcium ions.

In a further aspect, the present invention provides use of a single-strand DNA binding protein (SSB) which exhibits at least 50% of its maximum ssDNA binding capability in the presence of 500 mM of sodium ions, to dehybridize a DNA molecule, wherein the DNA molecule is present in or exposed to a solution containing one or more of the following:
   (i) at least 350 mM of sodium ions,
   (ii) at least 50 mM of potassium ions,
   (iii) at least 150 mM of magnesium ions, or
   (iv) at least 200 mM of calcium ions.

The SSB of the invention are able to dehybridize a partially hybridised ssDNA molecule, e.g. in the absence of said SSB the ssDNA molecule may have one or more duplex regions of at least 2, 4 or 6 paired nucleotides (i.e. 1, 2 or 3 or more hydrogen bonded pairs). In the presence of an SSB of the invention, a DNA molecule may have no duplex region(s), i.e. essentially no secondary structure.

A "partially hybridized" ssDNA molecule may be at least 5%, 10%, 20%, 30% or 40% hybridized, i.e. at least 5%, 10%, 20% etc. of its nucleotides are part of a duplex. Typically, no more than 60%, e.g. no more than 50% or 40% of the nucleotides are part of a duplex. In this context, "duplex" and "hybridisation" refer to internal regions within a single strand that through hydrogen bonding form duplex regions.

A target ssDNA molecule may typically be 20-5000 nucleotides in length, typically 20-3000, e.g. 30-1500 nucleotides in length.

In other embodiments, the DNA to be dehybridised is a dsDNA molecule. In such embodiments, some or alternatively all of the DNA duplex may be dehybridised. In PCR for example, SSB binds to the newly separated strands and is involved in the dehybridisation of a fairly small part of the duplex which allows for incorporation of new complementary nucleotides.

In sequencing methods, e.g. nanopore sequencing, the dsDNA target molecule may be very large, e.g. up to 200 kilobases (kb), or even 300 kb. Typically up to 50 kb or 100 kb, e.g. 50 bases to 300 kb, more usually 100 bases to 200 kb. The substrate for (e.g. nanopore) sequencing may be an RNA/cDNA hybrid.

A suitable method for analysing ability to bind ssDNA at different salt concentrations is shown in the Examples and Figures herein. Such a method can be used to establish whether a given SSB molecule exhibits at least 50% of its maximum ssDNA binding capability in the presence of 500 mM of sodium ions. A suitable method employs a molecular beacon made of ssDNA with a florescent dye and quencher moiety; fluorescence is dependent on the extent of SSB binding and the impact this has on hybridisation within a region of the molecular beacon and therefore on the proximity to each other of the dye and quencher.

Alternatively, or in addition, the SSB of the present invention (and employed in the methods and uses of the present invention) exhibit at least 40%, preferably at least 50% or 60%, of their maximum ssDNA binding capability in the presence of 250 mM of potassium ions, and/or in the presence of 150 mM of magnesium ions and/or in the presence of 200 mM of calcium ions.

Preferably the SSB of the present invention exhibit at least 60%, more preferably at least 70% of their maximum ssDNA binding capability in the presence of 500 mM of sodium ions.

In a further aspect the present invention provides use of a single-strand DNA binding protein (SSB) which exhibits at least 50% of its maximum ssDNA binding capability in the presence of 500 mM of sodium ions to prevent hybridisation of complementary ssDNA wherein the ssDNA is present in or exposed to a solution containing one or more of the following:
   (i) at least 350 mM of sodium ions,
   (ii) at least 50 mM of potassium ions,
   (iii) at least 150 mM of magnesium ions, or
   (iv) at least 200 mM of calcium ions.

In a further aspect the present invention provides a method of dehybridising a DNA molecule comprising contacting a DNA molecule which is present in or exposed to a solution containing one or more of the following:
   (i) at least 350 mM of sodium ions,
   (ii) at least 50 mM of potassium ions,
   (iii) at least 150 mM of magnesium ions, or
   (iv) at least 200 mM of calcium ions,
with a single-strand DNA binding protein (SSB) which exhibits at least 50% of its maximum ssDNA binding capability in the presence of 500 mM of sodium ions, wherein the SSB comprises the amino acid sequence of SEQ ID NO:1 or an amino acid sequence which is at least 75% identical to SEQ ID NO:1, or a functional fragment thereof.

In a further aspect the present invention provides a method of preventing hybridisation of complementary ssDNA comprising contacting ssDNA which is present in or exposed to a solution containing one or more of the following:
(i) at least 350 mM of sodium ions,
(ii) at least 50 mM of potassium ions,
(iii) at least 150 mM of magnesium ions, or
(iv) at least 200 mM of calcium ions,
with a single-strand DNA binding protein (SSB) which exhibits at least 50% of its maximum ssDNA binding capability in the presence of 500 mM of sodium ions, wherein the SSB comprises the amino acid sequence of SEQ ID NO:1 or an amino acid sequence which is at least 75% identical to SEQ ID NO:1, or a functional fragment thereof.

"Complementary ssDNA" includes internal regions of complementarity within a single strand of ssDNA, as well as two separate ssDNA molecules with a region or regions of complementarity. The region or regions of complementarity may extend along the whole or substantially all of the length of the molecule such that the two ssDNA molecules would naturally form a standard dsDNA duplex. The prevention of hybridisation may be partial or complete, partial hybridisation occurs for example in amplification reactions where it is only necessary for a small region of the duplex to be prevented from hybridising as the unzipping of the original duplex and generation of new complementary strands proceeds.

In some embodiments the reaction mixture, solution or washing buffer employed in the methods and uses defined above will contain at least 500 mM, at least 750 mM or at least 1000 mM of sodium ions.

In some embodiments the reaction mixture, solution or washing buffer employed in the methods and uses defined above will contain at least 100 mM, at least 300 mM, at least 600 mM or at least 1000 mM of potassium ions.

In some embodiments the reaction mixture, solution or washing buffer employed in the methods and uses defined above will contain at least 200 mM or at least 250 mM of magnesium ions.

In some embodiments the reaction mixture, solution or washing buffer employed in the methods and uses defined above will contain at least 150 mM, 200 mM or 300 mM of calcium ions.

The above concentrations are all considered high salt concentrations in the present context.

In some embodiments, the reaction mixture, solution or washing buffer employed in the methods and uses defined above will contain an organic salt, e.g. acetate or glutamate as well as one or more inorganic salts. In some embodiments the reaction mixture, solution or washing buffer employed in the methods and uses defined above will contain sodium and potassium ions at the levels discussed above, preferably also with magnesium and or calcium ions at the levels discussed above. Washing buffers may advantageously contain high concentrations of more than one salt, e.g. to disrupt protein complexes in a protein purification protocol or to remove DNA-binding proteins from a DNA sample. In some embodiments the reaction mixture, solution or washing buffer employed in the methods and uses defined above contains a chaotropic salt.

The present inventors have identified and characterised a SSB from the bacterium *Salinibacter ruber* (International Journal of Systemic and Evolutionary Microbiology [2002] 52, 485-491) and this protein and derivatives, fragments, variants and homologues thereof are particularly preferred according to the present invention.

The wild-type *S. ruber* SSB sequence is as follows:

```
                                               (SEQ ID NO: 1)
MARGVNKVILIGNLGDDPELRYTGSGTAVCNMSLATNETYTDSDGNEVQN

TEWHDVVAWGRLGEICNEYLDKGSQVYFEGKLQTRSWEDRDNNTRYSTEV

KAQEMMFLDSNRQGGADMDGFDQTRGDESLDQTRQEQPAGSSGPQPGQQA

SSGGEDEDTFEPDDDLPF
```

Thus, preferred SSB molecules according to the present invention (i.e. which exhibit at least 50% of their maximum ssDNA binding capability in the presence of 500 mM of sodium ions) comprise or consist of the amino acid sequence of SEQ ID NO:1 or an amino acid sequence which is at least 75% identical to SEQ ID NO:1, or a functional fragment thereof.

In preferred embodiments, the SSB of the invention comprises or consists of an amino acid sequence that is at least 75%, preferably at least 80%, 85%, 90% or 95%, e.g. at least 98% or 99% or 99.5%, identical to SEQ ID NO:1, or a fragment thereof.

In some embodiments, the SSB comprises an amino acid sequence that has single or multiple amino acid alterations (additions, substitutions, insertions or deletions) compared to SEQ ID NO:1. Such sequences preferably may contain up to 20, e.g. up to 10 or 5, preferably 1, 2 or 3, more preferably 1 or 2, altered amino acids. Substitutions can be with conservative or non-conservative amino acids. Preferably said alterations are conservative amino acid substitutions.

Preferably, the SSB comprises the amino acid sequence of SEQ ID NO:1 or a functional fragment thereof.

In a preferred embodiment, the SSB consists of the amino acid sequence of SEQ ID NO:1 or a functional fragment thereof. In a most preferred embodiment, the SSB consists of the amino acid sequence of SEQ ID NO:1.

Functional fragments of SSB are provided and encompassed by the terms "single-strand DNA binding protein" and "SSB" and "SSB of the invention". Functional fragments are fragments that are able to bind to ssDNA at the elevated salt concentrations defined herein. Thus they exhibit at least 50% of their maximum ssDNA binding capability in the presence of 500 mM of sodium ions. Active fragments will typically contain a functional part (e.g. all or substantially all) of the 75 amino acid C-terminal region responsible for octamer formation, more preferably active fragments contain a functional part (e.g. all or substantially all) of the 100 amino acid C-terminal region, more preferably of the 111 amino acid C-terminal region. As used anywhere herein, the term "substantially" in relation to a region of an amino acid or nucleotide sequence means at least 90%, preferably at least 95%, more preferably at least 99% of the length of the region concerned. The term "substantially free" means at least 90% free, more preferably at least 95% free, more preferably at least 99% free.

Functional fragments may be at least 140 amino acids in length. Preferred fragments are, at least 150, at least 160, at least 170 or at least 175 amino acids in length. The fragments are at least 75 or 80%, preferably at least 85% or at least 90%, more preferably at least 95% (e.g. at least 98% or 99% or 99.5%), or 100% identical to the corresponding portion of SEQ ID NO:1.

Thus functional fragments according to the present invention exhibit at least 50% of their maximum ssDNA binding capability in the presence of 500 mM of sodium ions.

All SSB (including functional fragments) according to the invention have a high affinity for ssDNA, in particular, they may have a dissociation constant (KD), measured as molar concentration (M) of binding to a 150 nucleotide ssDNA molecule in a buffer containing 10 mM of NaCl of no more than $10\times10^{-8}$ M, preferably no more than $5\times10^{-8}$M, and in some highly preferred embodiments less than $3\times10^{-8}$M. The Examples describe a suitable method of determining KD using Surface Plasmon Resonance. These values represent performance at a low salt concentration, as discussed elsewhere herein, the unique advantages of the SSB of the present invention are realised at high salt concentrations.

The present inventors have found that at a broad range of salt concentrations, including at moderate to high concentrations, SSB from S. ruber maintains its ability to bind to ssDNA (which may or may not be part of a molecule with a double stranded region or regions). As a consequence it maintains its ability to prevent hybridisation of ssDNA and to dehybridize DNA (which may be fully or partially hybridised and may be a ssDNA molecule with regions of secondary structure or may be a dsDNA molecule e.g. a naturally occurring duplex) at high salt concentrations. Separation of two complementary strands which form a stable double helix (e.g. as occurs during standard dsDNA replication) requires helicase as well as SSB to achieve dehybridization. On the other hand, SSB alone is able to render a ssDNA molecule with some duplex regions free of secondary structure.

As an alternative to the SSB of SEQ ID NO:1, the SSB from *Salinobacter iranicus* or *S. lutueus* (International Journal of Systematic and Evolutionary Microbiology [2012] 62, 1521-1527) or derivatives, fragments or variants thereof may be employed. Derivatives and variants of these molecules include those with sequence identity relationships (% identity) with wild type sequences which are the same as discussed herein in relation to *S. ruber*.

Single-stranded DNA secondary structure formation in solution is primarily due to Watson-Crick base pairing and base stacking. Both stability of such structures and the global rigidity of ssDNA increases profoundly in high-salt concentration solutions. Salt ions bind to the phosphate backbone, hindering ssDNA-ligand interactions driven mainly by electrostatic forces. Therefore, in the high-salt environment, changes in the biophysical properties of ssDNA can cause malfunction of cellular maintenance systems. It has been shown that for *E. coli* SSB, high salt concentrations prevent SSB function, or, if ssDNA-SSB nucleoprotein complex had already formed, cause hyper-condensation of the ssDNA-protein complex. It is known that in salt concentrations equal or lower than 20 mM of NaCl, *E. coli* SSB binds ssDNA in high-cooperativity mode, forming an elongated, filament-like nucleoprotein complex, and in salt concentrations between 20 and 200 mM of NaCl *E. coli* SSB tetramers create a "beads-on-string" structure in which tetramers bind with limited cooperativity, thus even at these salt concentrations and in the presence of ssDNA, oligomeric/polymeric quaternary structure is not observed with *E. coli* SSB.

Figure 3:
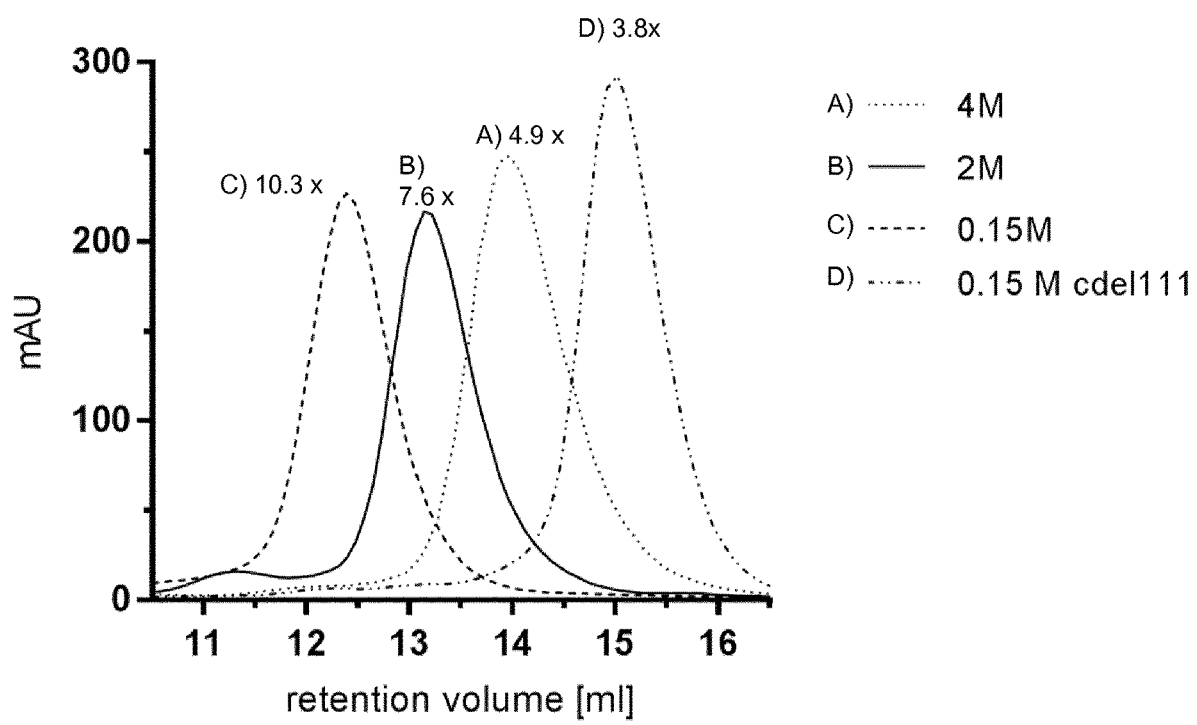
Figure 4:
Figure 4:
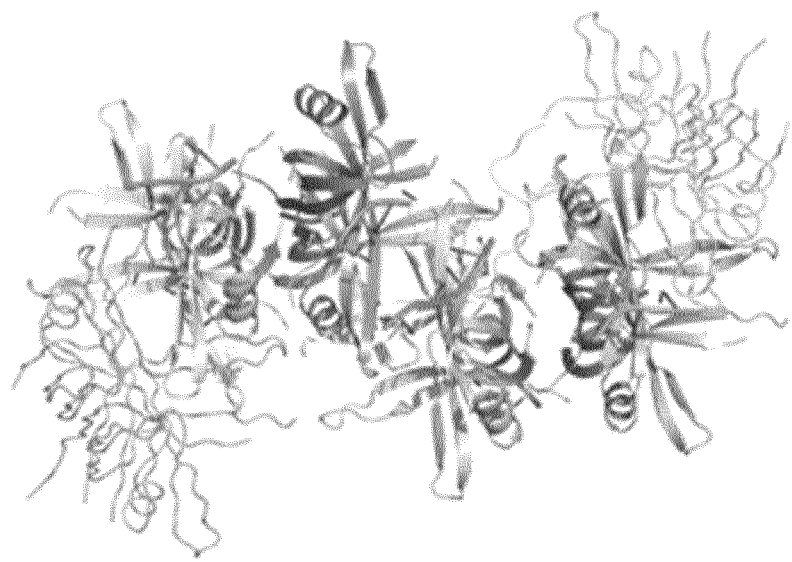
Figure 4:
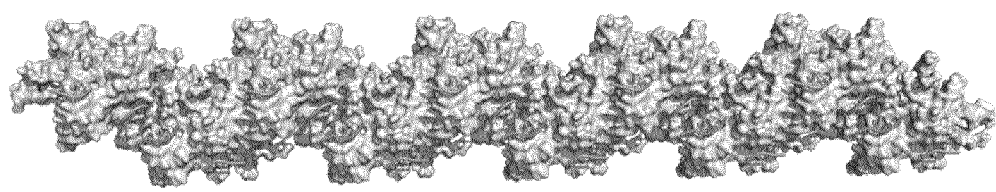

As shown in the Examples, the SSBs of the invention form octameric quaternary structure in the absence of ssDNA under high salt conditions (FIG. 3) and form polymeric quaternary structure under high salt conditions when bound to ssDNA (FIG. 2A, FIG. 4).

Under the salt conditions described herein, the SSB of the invention preferably has predominantly at least octameric quaternary structure in the absence of ssDNA. Preferably, the SSB of the invention has predominantly octameric quaternary structure in the absence of ssDNA at NaCl concentrations up to 2M. Under the salt conditions described herein, the SSB of the invention preferably has predominantly polymeric quaternary structure in the presence of ssDNA. As used herein, "predominantly" means that greater than 50% of the SSB proteins in a sample have the indicated oligomeric/polymeric state.

A "polymeric quaternary structure" is a term well-known in the art, used to indicate that a protein expressed as a monomer associates with multiple copies of the same protein to form a polymer.

Methods for determining the quaternary structure, i.e. oligomeric state, of a protein are well known in the art and any such method could be used to determine the quaternary structure, i.e. oligomeric state, of a SSB. For instance, as demonstrated in the Examples, size exclusion chromatography can be used to determine the average oligomer mass of a protein, thereby indicating the quaternary structure of that protein. Calibration using standard proteins with known molecular weights e.g. ferritine (440 kDa), aldolase (158 kDa), concalbumin (75 kDa) and ovalbumin (43 kDa), is well-known in the art.

An average oligomer mass above 10 times the size of the SSB monomer is indicative of a predominantly polymeric quaternary structure. An average oligomer mass above 6 times the size of the SSB monomer is indicative of a predominantly octameric quaternary structure.

Preferably, the SSB of the invention displays an average oligomer mass of at least 10 times the size of the SSB monomer at 0.15 M NaCl, and/or at least 6 times the size of the SSB monomer, more preferably at least 7 times the size of the SSB monomer at 2 M NaCl, as determined using size exclusion chromatography performed on a Superdex 200 column in a buffer containing 25 mM Tris, pH 7.5 and the stated NaCl concentration, with reference to standard proteins ferritine (440 kDa), aldolase (158 kDa), concalbumin (75 kDa) and ovalbumin (43 kDa).

The present inventors have surprisingly found that mutation of the wild type *S. ruber* SSB significantly increases its binding affinity for single strand nucleic acid. Thus preferred SSB molecules according to the invention incorporate either a substitution at position 17 or 71 or most preferably both. Substitution at position 71 is particularly preferred.

In a further aspect the present invention provides a single-strand DNA binding protein (SSB) which exhibits at least 50% of its maximum ssDNA binding capability in the presence of 500 mM of sodium ions and comprises the amino acid sequence of SEQ ID NO:1 or an amino acid sequence which is at least 75% identical thereto, or a functional fragment thereof, and wherein the amino acid at position 17 or 71 has been substituted.

In wild-type *S. ruber* SSB positions 17 and 71 are occupied by aspartic acid. The replacement amino acid preferably lacks a negative charge and preferably carries a positive charge (on its side chain) at pH 7.0. Suitable replacement amino acids include lysine, histidine, arginine, tyrosine, asparagine and glutamine, lysine and arginine are preferred and lysine is especially preferred.

It will be understood that positions 17 and 71 are defined with reference to the full length wild type sequence of SEQ ID NO:1. In some SSB molecules of the invention, through amino acid addition or deletion or selection of a different starting sequence, "positions 17 and 71" will be understood as the equivalent position when a standard sequence alignment is performed, i.e. the substituted residue may not be the $17^{th}$ or $71^{st}$ residue in that molecule.

These SSB (with substitution at position 17 and/or 71 or equivalent thereof) are referred to herein as mutated SSB and are preferred SSB for use in the methods and uses of the invention defined above. Preferred features of the SSB of the invention described above are also exhibited by these mutated SSB. For example, the mutated SSB preferably exhibit at least 40% of their maximum ssDNA binding capability in the presence of 250 mM of potassium ions, and/or 150 mM of magnesium ions. Preferably, the mutated SSB exhibit at least 60% or more preferably at least 70% of their maximum ssDNA binding capability in the presence of 500 mM of sodium ions. Preferably the mutated SSB exhibit at least 60% or more preferably at least 70% of their maximum ssDNA binding capability in the presence of chaotropic salts, in particular of chaotropic salts incorporating cations at high concentrations, as defined herein.

In preferred embodiments the mutated SSB comprises an amino acid sequence that is at least 80%, 85%, 90% or 95%, e.g. at least 98% or 99%, identical to SEQ ID NO:1, but with a substitution at position 17 and/or 71, or a functional fragment thereof incorporating said substitution(s).

In some embodiments, as well as mutation at position 17 or 71, the mutated SSB has single or multiple amino acid alterations (additions, substitutions, insertions or deletions) compared to SEQ ID NO:1. Such sequences preferably may contain up to 20, e.g. up to 10 or 5, preferably 1, 2 or 3, more preferably 1 or 2, altered amino acids. Substitutions can be with conservative or non-conservative amino acids. Preferably said alterations are conservative amino acid substitutions.

Preferably the amino acids at positions 17 and 71 are substituted as compared to SEQ ID NO:1.

In a particularly preferred embodiment, the mutated SSB of the invention comprises or consists of the amino acid of SEQ ID NO:1 but wherein the amino acid at position 17 or 71, preferably both, is lysine, as shown below.

(SEQ ID NO: 2)
MARGVNKVILIGNLGD<u>K</u>PELRYTGSGTAVCNMSLATNETYTDSDGNEVQN

TEWHDVVAWGRLGEICNEYL<u>K</u>KGSQVYFEGKLQTRSWEDRDNNTRYSTEV

KAQEMMFLDSNRQGGADMDGFDQTRGDESLDQTRQEQPAGSSGPQPGQQA

SSGGEDEDTFEPDDDLPF

Nucleic acid molecules that encode mutated SSB of the invention (including fragments thereof), or nucleic acid molecules substantially homologous thereto, form yet further aspects of the invention. A preferred nucleic acid molecule is a nucleic acid encoding the SSB of SEQ ID NO:1 but wherein the amino acid at position 17 or 71 has been replaced with an amino acid selected from lysine, arginine, tyrosine, asparagine and glutamine. A particularly preferred nucleic acid is one encoding the SSB of SEQ ID NO:2, for example the nucleic acid molecule depicted in SEQ ID NO:5. Degenerate versions of SEQ ID NO:5 will encode SEQ ID NO:2.

Nucleic acid molecules and proteins of the invention are preferably "isolated" or "purified".

Sequence identity may be assessed by any convenient method. However, for determining the degree of homology identity between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA,* 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.,* 48:443, 1970) as revised by Smith and Waterman (Smith and Waterman, *Adv. Appl. Math.,* 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.,* 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS,* 4:11-17, 1988), FASTA (Pearson and Lipman, *Proc. Natl. Acad. Sci. USA,* 85:2444-2448, 1988; Pearson, *Methods in Enzymology,* 183:63-98, 1990) and gapped BLAST (Altschul et al., *Nucleic Acids Res.,* 25:3389-3402, 1997), BLASTP, BLASTN, or GCG (Devereux, Haeberli, Smithies, *Nucleic Acids Res.,* 12:387, 1984) are also useful for this purpose. Furthermore, the Dali server at the European Bioinformatics institute offers structure-based alignments of protein sequences (Holm, *Trends in Biochemical Sciences,* 20:478-480, 1995; Holm, *J. Mol. Biol.,* 233:123-38, 1993; Holm, *Nucleic Acid Res.,* 26:316-9, 1998).

By way of providing a reference point, sequences according to the present invention having 65%, 70%, 75%, 80%, 85%, 90%, 95%, 96%, 97%, 98% or 99% sequence identity may be determined using the ALIGN program with default parameters (for instance available on Internet at the GENESTREAM network server, IGH, Montpellier, France).

A "conservative amino acid substitution", as used herein, is one in which the amino acid residue is replaced with another amino acid residue having a similar side chain e.g. positively charged, hydrophobic etc. Families of amino acid residues having similar side chains have been defined in the art.

SSB of the present invention comprise genetically encoded amino acids, but may also contain one or more non-genetically encoded amino acids or modified amino acids or N or C terminal modifications.

The term "isolated" or "purified" as used herein in reference to nucleic acid molecules or sequences and proteins or polypeptides, e.g., SSB, refer to such molecules when isolated from, purified from, or substantially free of their natural environment, e.g., isolated from or purified from an organism (if indeed they occur naturally) or host cell used for production, or refers to such molecules when produced by a technical process, i.e., includes recombinant and synthetically produced molecules.

Thus, when used in connection with a protein or polypeptide molecule such as SSB, the term "isolated" or "purified" typically refers to a protein substantially free of cellular material or other proteins from the source from which it is derived. In some embodiments, such isolated or purified proteins are substantially free of culture medium when produced by recombinant techniques, or chemical precursors or other chemicals when chemically synthesized.

In a further aspect the present invention provides an expression vector (preferably a recombinant expression vector) containing a nucleic acid molecule of the invention as defined above and the necessary regulatory sequences for the transcription and translation of the protein sequence encoded by the nucleic acid molecule of the invention.

Possible expression vectors include but are not limited to cosmids or plasmids, so long as the vector is compatible with the host cell used. The expression vectors are suitable for transformation of a host cell, which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and Maniatis, *Molecular Cloning: A Laboratory Manual*, 2nd Ed., Cold Spring Harbor Press, Cold Spring Harbor, N.Y., 1989) and other laboratory textbooks.

Suitable host cells include a wide variety of prokaryotic host cells and eukaryotic cells. Preferably, proteins of the invention may be expressed in bacterial host cells, such as *Escherichia coli*.

N-terminal or C-terminal fusion proteins comprising SSB of the invention conjugated to other molecules, such as proteins or peptides (e.g. epitope tags or purification tags), may be prepared by fusing through recombinant techniques.

SSB of the invention may also be conjugated to other moieties, e.g. reporter moieties such as those incorporating a fluorescent moiety. A fusion protein may comprise an SSB of the invention fused to a nucleic acid polymerase, said polymerase may be thermostable and/or halotolerant.

A yet further aspect provides a host cell or virus comprising one or more expression vectors of the invention. Also provided are host cells or viruses comprising one or more of the nucleic acid molecules of the invention. A host cell or virus capable of expressing a SSB of the invention forms a yet further aspect.

Where appropriate, SSB of the invention may be isolated from a natural source, e.g. isolated from extracts of a Salinobacter, or produced recombinantly in a host cell and isolated and purified therefrom. In certain embodiments the SSB is produced by recombinant techniques in a host cell that is not, or not from, an organism which is the same as that in which the SSB is found naturally, i.e. a heterologous host cell.

The present inventors have prepared a codon optimised version of the wild type *S. ruber* SSB gene and that is designated herein as SEQ ID NO:4. Nucleic acid molecules comprising the nucleic acid sequence of SEQ ID NO:4 or a functional fragment thereof constitutes a further aspect of the present invention. Functional fragments are those encoding functional fragments of SSB as defined above. Nucleic acid molecules comprising the nucleic acid sequence of SEQ ID NO:5 are codon optimised and incorporate the codons for lysine at positions 17 and 71 and is a preferred embodiment of the present invention.

SSB of the present invention may be generated using recombinant DNA technology. Alternatively, a cell-free expression system can be used for production of the SSB. Alternatively, SSB of the present invention may be generated using chemical synthesis by stepwise elongation, one amino acid at a time. Such chemical synthesis techniques (e.g. solid phase synthesis) are well known in the chemistry of proteins.

A further aspect of the invention provides a method of producing a SSB (including mutated SSB) of the present invention comprising a step of culturing the host cells of the invention. Preferred methods comprise the steps of (i) culturing a host cell comprising one or more of the recombinant expression vectors or one or more of the nucleic acid molecules of the invention under conditions suitable for the expression of the encoded SSB; and optionally (ii) isolating or obtaining the SSB from the host cell or from the growth medium/supernatant. Such methods of production may also comprise a step of purification of the SSB and/or formulating the SSB into a composition or product including at least one additional component, such as an appropriate buffer or carrier.

The SSB may be separated, or isolated, from the host cells/culture media or natural source using any of the purification techniques for protein known in the art and widely described in the literature or any combination thereof. Such techniques may include for example, precipitation, ultrafiltration, dialysis, various chromatographic techniques, e.g. gel filtration, ion-exchange chromatography, affinity chromatography, electrophoresis, centrifugation etc. As discussed above, the SSB of the invention may be modified to carry amino acid motifs or other protein or non-protein tags, e.g. polyhistidine tags, to assist in isolation, solubilisation and/or purification or identification.

As discussed above, one aspect of the present invention is a method of nucleic acid sequencing. In preferred embodiments, these methods are next-generation sequencing methods. So-called "next generation", or "second" or "third generation" sequencing approaches (in reference to the Sanger dideoxynucleotide method as the "first generation" approach) have become widespread. These newer techniques are characterised by high throughputs, e.g. as a consequence of the use of parallel, e.g. massively parallel sequencing reactions, or through less time-consuming steps. Various high throughput sequencing methods provide single molecule sequencing and employ techniques such as pyrosequencing, reversible terminator sequencing, cleavable probe sequencing by ligation, non-cleavable probe sequencing by ligation, DNA nanoballs, Single Molecule, Real-Time sequencing (SMRT) and nanopore sequencing.

Salt-stable nucleoprotein complexes, as may be generated according to the methods and uses of the present invention, can withstand washing with high-salt buffers. This is very useful in next generation sequencing, as described in the following process. During solid phase DNA amplification, which generates clusters of surface-bound DNA oligonucleotides, a number of washes are used. The purpose of the washing steps is to remove the unbound template and limit the annealing of non-complementary templates to the surface-attached oligos. Most of these washing solutions contain high concentrations of salt. By introducing salt active SSB protein, the DNA is kept single stranded throughout the washing cycle, thus cannot form secondary structures that decrease the activity of many DNA-processing enzymes. It has been shown that the addition of SSB proteins increased the fidelity and processivity of DNA polymerases (Nucleic Acids Res 31(22): 6473-6480). These parameters are crucial during the cluster generation process and ensure that the following sequencing phase is performed as efficiently as possible.

High salt washes are also incorporated into Sequencing-by-Synthesis which is a core process of the second generation of high-throughput sequencing. In order to prevent the disruption of the following cycle, the excess of nucleotides and other components, such as cleaved-off synthesis inhibitors, cleavage enzymes etc., are removed in the washing step. Again, SSB protein that can keep the DNA in a single stranded form throughout the washing procedures, would greatly improve the quality of sequencing.

Thus preferred sequencing methods of the present invention include a solid phase DNA amplification step and/or a sequencing-by-synthesis step.

Nanopore sequencing is known as a "third generation" sequencing method and is a particularly preferred sequencing method of the present invention. Nanopore sequencing utilizes the different effect on current across a pore which is observed as each of nucleotides A, T, C and G pass through the pore (Wang et al. (2015) Frontiers in Genetics, Vol 5, Article 449). A nanopore is a hole with an internal diameter of no more than about a nanometer (e.g. 2 nm), the pore being formed of organic or inorganic material, such as transmembrane proteins, silicon or graphene. Typically, a dsDNA molecule is sequenced by the passage of one of its strands through the pore, each nucleotide causes a readable change in current across the pore. SSB may be helpful when bound either to the strand which is upstream of the pore and has not (yet) been sequenced and/or to the strand which has passed through the pore.

Thus, a preferred embodiment of the invention is a method of nanopore sequencing wherein the sample solution contains a single-strand DNA binding protein (SSB) which exhibits at least 50% of its maximum ssDNA binding capability in the presence of 500 mM of sodium ions; preferably the SSB is the *S. ruber* SSB or a derivative, fragment, variant or homologue thereof. Thus the SSB preferably has the amino acid sequence of SEQ ID NO:1 or an amino acid sequence which is at least 75% identical to SEQ ID NO:1 or is a functional fragment thereof as defined above.

A particularly preferred "second generation" sequencing method of the present invention is pyrosequencing in which the SSB may increase signal intensity, decrease nonspecific signals, improve polymerization efficiency, reduce non-quantitative signals and/or reduce inhibition of the enzymes apyrase and polymerase. Pyrosequencing is an example of a method of sequencing-by-synthesis which is based on the detection of pyrophosphate which is released on nucleotide incorporation.

As discussed above, an aspect of the present invention is a method of nucleic acid amplification. Typically, said method comprises providing a reaction mixture comprising a DNA polymerase, an SSB of the invention as defined above, a template nucleic acid molecule, an oligonucleotide primer(s) (e.g. 2 or more primers such as 2, 3, 4, 5 or 6 primers) which is capable of annealing to a portion of the template nucleic acid molecule acid molecule, and nucleotides (e.g. deoxynucleoside triphosphates, dNTPS) and incubating said reaction mixture under conditions whereby the oligonucleotide primer(s) anneals to the template nucleic acid molecule and said DNA polymerase extends said oligonucleotide primer(s) by polymerising one or more nucleotides to generate a polynucleotide. Suitable conditions are well known in the art. Preferred methods of nucleic acid amplification are isothermal amplification methods, although the amplification methods of the invention include PCR (and RT-PCR). Isothermal amplification methods of the invention are performed at a constant temperature and preferred temperatures are set out elsewhere herein. Optionally, the generation of the polynucleotide product is detected (e.g. via gel electrophoresis).

Exemplary isothermal amplification methods include Loop mediated isothermal amplification (LAMP), rolling circle amplification (RCA), strand displacement amplification (SDA), helicase dependent amplification (HDA), multiple displacement amplification (MDA) and cross priming amplification (CPA).

As discussed above, an aspect of the present invention is a method of site-directed-mutagenesis. Such a method may employ a DNA primer comprising the desired mutation(s) which is otherwise complementary to the template DNA around the mutation site. When the primer is annealed to the template in the reaction mixture, which further comprises an SSB as defined herein, a DNA polymerase is then used to extend the primer. The reaction mixture typically also comprises the protein Rec A. The copy of the template sequence incorporates the desired mutation and this may be inserted into a vector and introduced into a host cell and cloned.

Uses and methods of the present invention are typically performed in vitro.

The present invention also provides compositions comprising an SSB of the invention as defined above. Such compositions preferably comprise a buffer and a stabilising agent such as glycerol or sucrose and may also comprise a DNA polymerase. Compositions may be aqueous and buffered with a standard buffer such as Tris, HEPES, etc. In some embodiments the buffer containing the SSB may contain high salt concentrations, e.g. at least 350 mM of sodium ions, at least 50 mM of potassium ions, at least 150 mM of magnesium ions and/or at least 200 mM of calcium ions. Thus the SSB of the invention may advantageously be included in such a high salt washing buffer. A suitable formulation for the SSB of the invention as defined above comprises 25 mM Tris-Cl at pH 8.0, 200 mM NaCl and 10% glycerol.

The invention further includes kits comprising one or more of the SSB of the invention as defined above, or one or more compositions of the invention, or one or more of the nucleic acid molecules of the invention, or one or more expression vectors of the invention, or one or more host cells or viruses of the invention. Preferably said kits are for use in the methods and uses as described herein, e.g., in nucleic acid amplification or sequencing methods, such as nanopore sequencing methods. Preferably said kits comprise instructions for use of the kit components, for example for nucleic acid amplification or sequencing. Thus the kit may further comprise one or more of a polymerase, a washing or other buffer (which may contain a high salt concentration as discussed further herein), nucleotides, nucleic acid primers, a ligase, topoisomerase or gyrase (or other molecular motor protein to assist with nanopore sequencing).

In a further aspect the present invention provides an SSB of the invention as defined above, or a composition of the invention, contained within a cartridge which is suitable for use in a sequencing device, e.g. a MinION or GridION (Oxford Nanopore Technologies).

The invention is further described in the following non-limiting examples and with reference to:

FIG. 1 A), B), C) and D) which show binding of S. ruber SSB (wild-type and mutant forms) and E. coli SSB to DNA in the presence of monovalent and divalent salts.

Figure 2:
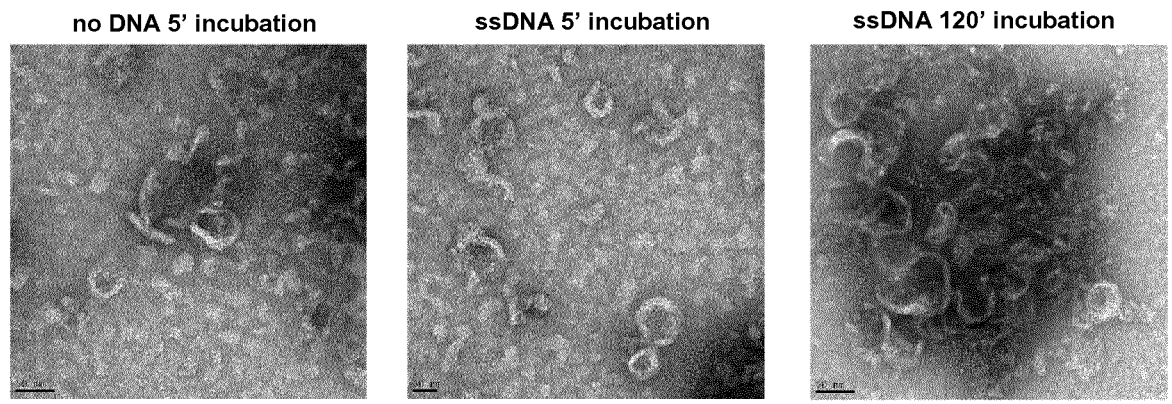
Figure 2:
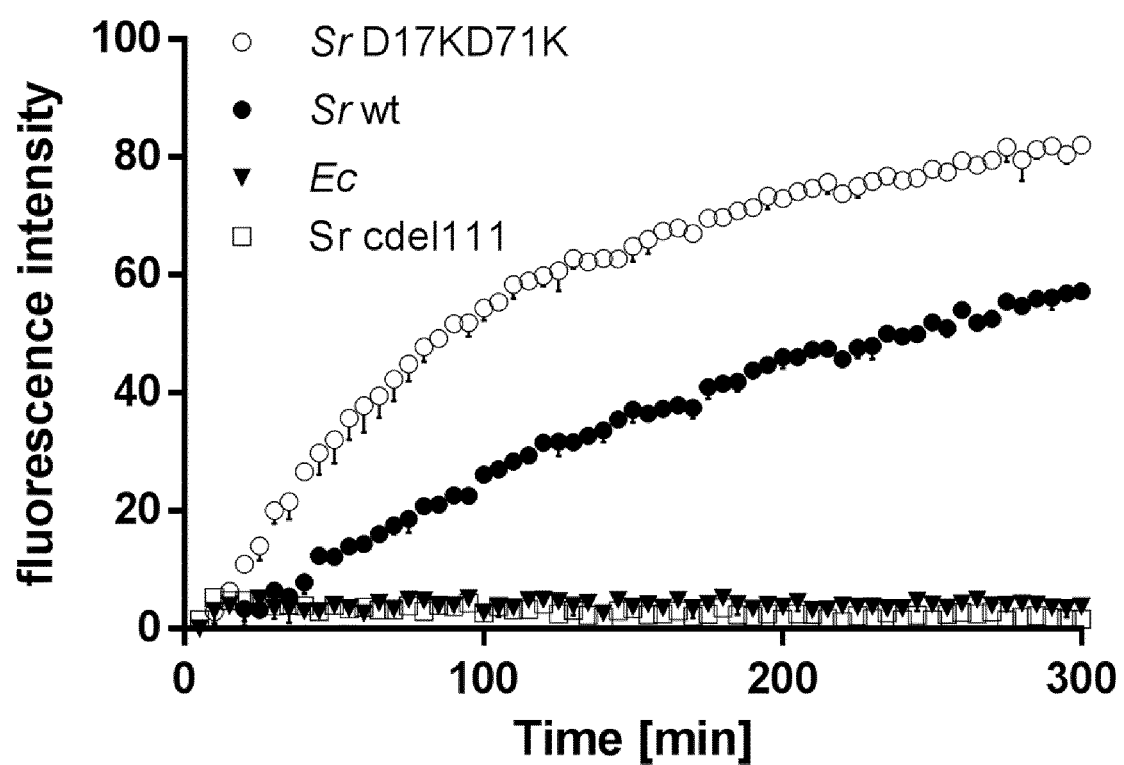

FIG. 2 A) which shows SrSSB D17KD71K mutant in the presence of a mixture of salts (350 mM NaCl, 600 mM KCl and 150 mM Mg(OAc)$_2$) without ssDNA or incubated with M13 phage ssDNA for 5 or 120', visualized with electron microscopy; B) which shows binding of S. ruber SSB (wild-type and mutant forms) and E. coli SSB to DNA in the presence of a mixture of salts (350 nM NaCl, 600 nM KCl and 150 nM Mg(OAc)$_2$).

FIG. 3 which shows the apparent oligomer mass of S. ruber wildtype SSB determined using size exclusion chromatography at 0.15M, 2 M and 4 M NaCl, and the S. ruber SSB cdel 111 terminal deletion mutant, determined using size exclusion chromatography at 0.15M NaCl.

FIG. 4 which shows the crystal structure of S. ruber SSB in high salt conditions. The structure shows filament-like architecture consisting of polymerized tetramers. (A) Polymerization interface is formed by two adjacent dimers belonging to separate tetramers and repeated along the filament. (B) Crystal packing of tetramers in the filament. Short DNA fragments of bound DNA are soaked-in (dT)8 oligonucleotides.

EXAMPLES

Identification and Cloning of Wt S. ruber SSB and D17K D71K Mutant

The single SSB open reading frame was identified in S. ruber strain DSM 13855 genome (GenBank: CP000160.1) by using blastp algorithm with E. coli SSB sequence as query (NCBI: WP_042201710.1) (J. Mol. Biol [1990] 215, 403-410). Two point mutations that substitute aspartic acid to lysine in positions 17 and 71 were introduced, yielding the D17K D71K mutant.

Genes encoding wild-type SSB and D17K D71K mutant were synthesized with codon optimization for expression in E. coli (using DNA 2.0). In the codon-optimized genes 26% of the original nucleotides were replaced and the GC-content was changed from the original 63% to 47%, which made the resulting genes better suited for expression in E. coli.

TABLE 1 gene sequences

| SEQ ID No. | NAME | SEQUENCE |
|---|---|---|
| 3 | wt SrSSB Coding Sequence (CDS) | 5'-ATGGCACGCGGAGTCAACAAGGTCATTCTC ATCGGCAACCTCGGCGACGATCCCGAACTGCGG TACACCGGCAGCGGGACGGCTGTCTGCAACATG TCGCTCGCGACCAACGAAACCTACACCGATAGC GACGGCAATGAGGTGCAAAACACCGAGTGGCAC GACGTCGTGGCGTGGGGCGGCTCGGAGAGATC TGCAACGAGTACCTTGACAAGGGCTCCCAGGTC TACTTCGAGGGCAAGCTCCAAACCCGCTCTTGG GAGGACCGCGACAACAACACGCGCTACTCGACG GAGGTGAAGGCCCAAGAGATGATGTTCCTCGAC AGCAATCGCCAGGGCGGGGCGGACATGGACGGC TTCGACCAGACCCGTGGGGACGAATCCCTGGAC CAAACCCGCCAGGAGCAGCCCGCCGGCTCTTCC GGTCCGCAGCCTGGGCAGCAGGCGTCCTCCGGG GGCGAGGACGAGGACACATTCGAGCCGGACGAT GATCTTCCGTTCTAG-3' |
| 4 | wt SrSSB codon optimized, synthetic gene | 5'-ATGGCACGTGGTGTGAATAAAGTGATTCTG ATTGGTAATCTGGGTGATGATCCGGAACTGCGT TATACCGGTAGCGGCACCGCAGTTTGTAATATG AGCCTGGCAACCAATGAAACCTATACCGATAGT GATGGTAATGAAGTGCAGAATACCGAATGGCAT GATGTTGTTGCATGGGGTCGTCTGGGTGAAATT TGTAATGAATATCTGGATAAAGGCAGCCAGGTG TATTTTGAAGGTAAACTGCAGACCCGTAGCTGG GAAGATCGTGATAATAACACCCGTTATAGCACC GAAGTTAAAGCCCAAGAAATGATGTTTCTGGAT AGCAATCGTCAGGGTGGTGCAGATATGGATGGT TTTGATCAGACCCGTGGTGATGAAAGCCTGGAT CAGACACGTCAAGAACAGCCTGCAGGTAGCAGC GGTCCGCAGCCTGGTCAGCAGGCAAGCAGCGGT GGTGAAGATGAAGATACCTTTGAACCGGATGAT GATCTGCCGTTT-3' |
| 5 | SrSSB D17K D71K | 5'-ATGGCACGTGGTGTGAATAAAGTGATTCTG ATTGGTAATCTGGGTGATAAACCGGAACTGCGT TATACCGGTAGCGGCACCGCAGTTTGTAATATG AGCCTGGCAACCAATGAAACCTATACCGATAGT GATGGTAATGAAGTGCAGAATACCGAATGGCAT GATGTTGTTGCATGGGGTCGTCTGGGTGAAATT TGTAATGAGTACTTGAAAAAAGGCAGCCAGGTG TATTTTGAAGGTAAACTGCAGACCCGTAGCTGG GAAGATCGTGATAATAACACCCGTTATAGCACC GAAGTTAAAGCCCAAGAAATGATGTTTCTGGAT AGCAATCGTCAGGGTGGTGCAGATATGGATGGT TTTGATCAGACCCGTGGTGATGAAAGCCTGGAT CAGACACGTCAAGAACAGCCTGCAGGTAGCAGC GGTCCGCAGCCTGGTCAGCAGGCAAGCAGCGGT GGTGAAGATGAAGATACCTTTGAACCGGATGAT GATCTGCCGTTT-3' |

Constructs for expression of SrSSB protein variants in E. coli were cloned with a Fast Cloning method (BMC Biotechnol [2011] 11, p 92). Insert fragments were generated by PCR reaction with SrSSB i FW (forward) and SrSSB i RW (reverse) oligonucleotides with wt SrSSB or SrSSB D17K D71K synthetic genes as templates. The vector fragment was generated by PCR reaction with SrSSB v RW and SrSSB v FW oligonucleotides with pCOLD II expression vector (Takara) as template. For the removal of template DNA DpnI restriction enzyme was added and fragments were mixed and incubated for 3 h at 37° C. The mixture was than transformed NovaBlue competent cells (Novagene), yielding constructs for expression of both genes in E. coli cells.

For generation of both inserts and the vector fragment Phusion High-Fidelity DNA Polymerase (Thermo) was used. Oligonucleotides used for gene cloning were synthesized by Integrated DNA Technologies. Cloned constructs were verified by DNA sequencing.

TABLE 2 oligonucleotides

| SEQ ID No. | NAME | SEQUENCE |
|---|---|---|
| 6 | SrSSB i FW | 5'-CTTTACTTCCAGGGGGCCATGGCACGTGGTGTGAAT-3' |
| 7 | SrSSB v RW | 5'-ATTCACACCACGTGCCATGGCCCCCTGGAAGTAAAG-3' |
| 8 | SrSSB v FW | 5'-GATGATCTGCCGTTTTAATGAGGATCCGAATTCAAG-3' |
| 9 | SrSSB i RW | 5'-CTTGAATTCGGATCCTCATTAAAACGGCAGATCATC-3' |
| 10 | MB | 5'-<u>GGCCCG</u>[S1]AGGAGGAAAGGACATCTTCTAGCA[S2]A<u>CGGGCC</u>GTCAAGTTCATGGCCAGTCAAGTCGTCAGAAATTTCGCACCAC-3'<br>[S1] = [dt-DABCYL]<br>[S2] = [dt-FAM]<br>FAM = carboxyfluorescein<br>DABCYL = 4-(4'-dimethylaminophenylazo) benzoic acid<br>Underlined complementary bases form a 8 base pair, double-stranded stem |
| 11 | SPR 150nt | 5'-(BTN)-AAAGGGTATTGACGGACCAGATGTAGCGTGGCAGAAAAGGGTATTGACGGACCAGATGTAGCGTGGCAGAGACTGAAAGGGTATTGACGGACCAGATGTAGCGTGGCAGAAAAGGGTATTGACGGACCAGATGTAGCGTGGCAGAGACTG-3'<br>BTN = biotin |

Protein Expression and Purification

E. coli cells strain B121 transformed with wt SrSSB expression plasmid were grown overnight, than diluted 1:50 with fresh Terrific Broth medium supplemented with ampicillin (100 mg/ml). Cells were cultivated until OD600 reached 0.5 then cultures were cooled down to 18° C. Recombinant protein expression was induced by addition of 0.5 mM IPTG and cultivation was continued at 18° C. overnight. The cells were than harvested by centrifugation (8000×g, 4° C., 10 min), and resuspended in buffer A (Tris-HCl 25 mM pH 7.4, NaCl 0.5 M, imidazole 10 mM, 3-mercaptoethanol 5 mM, Tween 20 0.05%, glycerol 10%). After disruption of cells in a French press (27 kpsi applied) the crude extract was clarified by centrifugation (65,000×g, 4° C., 30 min.) and supernatant was used for protein purification by Immobilized Metal Affinity Chromatography (IMAC) with a 1 mL HisTrap HP column (GE Healthcare). Prior to loading the column was equilibrated with 5 column volumes (CV) of buffer A. After the clarified lysate was applied to the column, unbound material was removed by a 5 CV wash with buffer A. Protein was than eluted in a linear gradient from 10 mM to 500 mM imidazole in 10 CV of buffer A. Fractions containing SSB were detected by SDS-PAGE, after which they were combined and concentrated using Amicon Ultra-15 Filter Device with molecular weight cut-off of 100 kDa (Millipore, USA). Final dialysis was performed against buffer B (Tris-HCl 25 mM pH 7.4, NaCl 0.15 M, β-mercaptoethanol 5 mM, glycerol 10%). The purification of D17K D71K mutant was performed according to the same protocol. The purity of purified SSB proteins was estimated using SDS-PAGE (at over 95%), concentration was measured fluorometrically.

Single-Strand DNA Binding Activity Measurements
Fluorescence Measurements

Wild-type S.ruber SSB and the D17K D71K mutant were tested for their ability to bind ssDNA in reaction buffer supplemented with NaCl, KCl, $MgCl_2$ and $CaCl_2$. E. coli SSB was used as a well characterized, reference protein.

In the assay a change of fluorescence of a fluorophore-labelled oligonucleotide (Table 2, SEQ ID NO:10) is being detected. The oligonucleotide MB is designed to form a partial hairpin with a short, eight base pair (bp) double-strand stem and a 24 base single-strand loop. The oligo is labeled with a fluorescent dye-FAM (carboxyfluorescein and DABCYL (4-(4'-dimethylaminophenylazo) benzoic acid) which quenches FAM fluorescence. When the oligonucleotide is in its native, hairpin state both 5' and 3' ends of the stem are in proximity and FAM fluorescence is quenched by DABCYL. Binding of SSB protein to the 24 nucleotide loop disrupts the hydrogen bonds in the double-strand stem and forces dehybridization of the oligonucleotide. Spatial separation of FAM and DABCYL allows measurement of dye fluorescence (Tang et al. Chemical Communications [2011] 47 (19), p 5485-5487)].

Both the wild-type and the D17K D71K mutant proteins are able to efficiently bind and dehybridize the fluorescent probe in high salt concentrations of both mono- and divalent salts. The nucleoprotein complex formation with ssDNA probe in the presence of sodium chloride (NaCl), potassium chloride (KCl) and magnesium chloride ($MgCl_2$) in ranges from 10 mM to 1M, 0M to 1M and 0M to 250 mM respectively, is shown in FIG. 1 A-C.

Reactions contained 0.125 μM of molecular beacon and 0.25 μM of E. coli SSB tetramer (single binding unit), 4 μM of wt SrSSB and 2 μM of D17K D71K. Reaction mixtures were set up in triplicates in 50 μl of reaction buffer MB (10 mM Tris-HCl pH 7, 10 mM NaCl) containing the fluorescent probe and supplemented with an indicated concentration of NaCl, KCl or $MgCl_2$ in 96-well plate (Corning). The binding reaction was initiated by addition of the indicated SSB protein, next reactions were incubated at 25° C. for 15' and the fluorescence was measured with excitation at 495 nm and emission at 520 nm on the Gemini plate reader (Molecular Devices). All graphs were normalized to 100% of initial response, measured in fluorescence units.

With the increasing concentration of sodium chloride, potassium chloride and magnesium chloride both SrSSB variants maintain their ability to bind and dehybridize ssDNA. The D17K D71K mutant shows levels of binding very similar to wt protein but at only half of the concentration, which indicates its increased affinity to ssDNA.

When increasing salt concentrations from 200-400 mM (for NaCl), binding affinity of previously described E. coli SSB protein drops drastically (Biochemistry [1988] 27, 456-471). This drop is due both to disruption of electrostatic interactions between the protein and the nucleic acid and the increasing stability of segments of double-strand DNA formed by complementary ssDNA. Consistent with previous observations, the affinity of reference SSB from E. coli to ssDNA decreased significantly with the increased concentration of all tested salts.

This experiment was also performed to test the susceptibility of E. coli, wild type and mutant S. ruber SSB to increased concentrations of $CaCl_2$. The results are shown in FIG. 1D.

Surface Plasmon Resonance

Higher binding affinity of the D17K D71K mutant was also confirmed by probing the protein-ssDNA interaction strength directly with the use of Surface Plasmon Resonance on a T200 instrument (BIACORE). This biosensor-based technique enables real-time measurement of binding parameters that enables calculation of equilibrium dissociation constant (KD) of different complexes, including nucleoprotein complexes. To ensure that the measurement is not biased by nucleotide sequence, a randomly generated, 150 nucleotide, 5'-biotynylated ssDNA oligonucleotide was used (Table 2, SEQ ID NO:11). Oligonucleotides were attached to the surface of the SA S-type chip (BIACORE) via biotin-streptavidin interaction. Next, both proteins were run in dilutions: 10 nM, 20 nM, 40 nM, 100 nM, 150 nM, 200 nM, 300 nM over the chip surface in MB buffer (10 mM Tris-HCl pH 7, 10 mM NaCl). The binding event was detected by mass change on the chip surface, which enabled real time measurements of the kinetic parameters of protein-ssDNA interaction. The kinetic parameters are given in the table in Table 3.

TABLE 3

| S. ruber SSB version | KD | Chi$^2$ |
|---|---|---|
| Wt | 3.43 × 10$^{-8}$ M | 0.529 |
| D17K D71K | 1.91 × 10$^{-8}$ M | 0.624 |

Table 3 gives dissociation constants (KD) of binding to the 150 nt single-strand DNA and quality of the fitting to the binding model of wild-type protein and D17D71K S. ruber SSB. Chi$^2$ values below 1 indicate a very good fit of the experimental data to the model used for KD calculation. KD of the D17KD71K mutant is over 1.8 fold lower, which indicates increased binding affinity of the mutated protein.

The decrease of KD value confirms that the introduction of D17K D71K mutations significantly increases the initial, already high, affinity of the wild-type SSB protein to the single-strand DNA.

This experiment was necessarily performed at a low salt concentration but is nonetheless indicative of the superior binding affinity of the mutant protein.

Binding and Dehybridization Fluorescent Assay in a Mixture of Salts

Wild-type S.ruber SSB, the D17K D71K mutant, and an S. ruber SSB cdel111 C-terminal deletion mutant lacking the C-terminal 111 residues of the wildtype SSB, were each tested for their ability to bind ssDNA in reaction buffer containing a mixture of NaCl, KCl and Mg(OAc)$_2$. E. coli SSB was used as a well characterized reference protein. Reactions contained 0.125 µM of molecular beacon, 0.25 µM of E. coli SSB tetramer (single binding unit), 4 µM of wt SrSSB, D17KD71K mutant octamer or cdel111 mutant. Reactions were set up in triplicates in 100 µl of reaction buffer MB (10 mM Tris-HCl pH 7) containing 350 mM NaCl, 600 mM KCl and 150 mM Mg(OAc)$_2$ in a 96-well plate (Corning) and incubated at 25° C. for 5 h. Fluorescence was measured with excitation at 495 nm and emission at 520 nm every 5 min. The baseline fluorescence of the reaction containing molecular beacon was subtracted. Measurements were performed on the Gemini microplate plate reader (Molecular Devices).

In the course of the experiment, we observed an increase of fluorescence for both wt and mutant S. ruber SSB, indicating binding of the protein to the DNA probe. The D17KD71K mutant had a significantly increased affinity towards ssDNA in the highly concentrated salt mixture. E. coli SSB and cdel111 had no measurable binding activity under experimental conditions. The results are shown in FIG. 2B.

Unlike E. coli SSB, which tetramers lose stability in relatively low concentrations of divalent salts, e.g., magnesium chloride, SrSSB is able to maintain its conformation and bind ssDNA in a mixture of highly concentrated mono- and divalent salts (FIG. 2).

Electron Microscopy of SrSSB-ssDNA Complexes

The SrSSB D17KD71K mutant protein was incubated in the same reaction conditions as under "Binding and dehybridization fluorescent assay in the salts mixture" alone or with ssDNA (M13mp18 Single-stranded DNA, NEB) in 200× excess. Protein concentration was 17 µM (octamer), incubation times varied from 5 to 120 minutes. To prepare the samples for Negative Stain Electron Microscopy, a 3 microliter drop of the analyte was place into a carbon coated grid for 1 min. then blotted away. The grid was washed 5 times with Mili-Q water, blotted off and the stained with 2% uranyl acetate for 1 min. The grid than was blotted and dried in vaccum for observation in a JEOL 1200 EXII in a low dose mode, operated at an acceleration voltage of 100 kV.

The EM visualizations are shown in FIG. 2A. When the protein alone or in a reaction mixture with M13 phage ssDNA was incubated for 5', a limited amount of highly ordered, ring-like and sickle-like structures could be observed. When the incubation was prolonged to 120' a high amount of large, ordered structures could be observed. The observed extensive structures are nucleoprotein complexes of SrSSB-ssDNA, which form extensively when the protein is incubated with ssDNA. It is therefore confirmed that the protein is able to form large, ordered, filament-like nucleoprotein complexes and bind and dehybridize ssDNA a highly concentrated salt solutions.

Oligomeric Structure

Sequence alignment of Salinibacter ruber (SrSSB) to the other known SSB suggested that the protein forms tetramers like the majority of bacterial SSBs, however during the initial characterization of the SrSSB, it was discovered that the protein exists in an unexpected, higher oligomeric state.

It has been shown that for E. coli SSB, high salt concentrations prevent SSB function, or, if ssDNA-SSB nucleoprotein complex had already formed, cause hyper-condensation of the ssDNA-protein complex. It is known that in salt concentration equal or lower than 20 mM of NaCl, E. coli SSB binds ssDNA in high-cooperativity mode, forming elongated, filament-like nucleoprotein complex, and in salt concentration between 20 and 200 mM of NaCl E. coli SSB tetramers create a "beads-on-string" structure in which tetramers bind with limited cooperativity.

To determine the assembly state of SSB from Salinibacter ruber in high and low salt conditions, a recombinantly produced SrSSB was analyzed by size exclusion chromatography and differential scanning calorimetry. In order to investigate the effect of salt concentration on SSB oligomeric state, SSB oligomer molecular mass estimation was made via size exclusion chromatography on a Superdex 200 10/300 GL column (GE healthcare). The analysis was performed in buffer C, containing 25 mM Tris pH 7.5 and 0.15M (buffer C1), 2M (buffer C2), 4M (buffer C3) NaCl. The elution pattern of wildtype S. ruber SSB protein was then compared with those of standard proteins: ferritine (440 kDa), aldolase (158 kDa), concalbumin (75 kDa), ovalbumin (43 kDa).

The results are shown in FIG. 3. Analysis of purified SrSSB by size exclusion revealed a single peak corresponding to a molecular mass of approximately 225 kDa, which is about 10.3 times the molecular mass of a monomer. This result indicates that the protein forms larger oligomers than previously described SSBs and that the SrSSB tetramers most probably assemble to octamers (dimers of tetramers), dodecamers (trimers of tetramers) and higher oligomeric states as multiples of four. The observed mass of 10.3 times of a monomer, therefore, represents a mixture of approximately 42% octamer and 58% dodecamer in equilibrium. With an increase in salt concentration, the size of the observed oligomer decreased to approximately 7.6 (~90% octamer, 10% tetramer) and 4.9 (~25% octamer, 75% tetramer) times the size of the monomer at 2M and 4M of NaCl respectively. Analysis of the oligomeric state was also performed in the presence of 500 mM $MgCl_2$, where the protein oligomer size was approximately 8 times the size of the monomer (data not shown).

Thus, the *S. ruber* SSB displays marked quaternary structure stability in the presence of high salt conditions even in the absence of ssDNA. Such quaternary structure is required for binding to ssDNA. A C-terminal deletion mutant of *S. ruber* SSB was shown not to bind ssDNA in the mixture of highly concentrated salts (FIG. 2B), and was shown to have an estimated size of 3.8×the size of the monomer (indicative of only tetrameric quaternary structure) at 150 mM NaCl (FIG. 3).

Surprisingly, unlike the wt SSB, the C-terminal deletion mutant CΔ111 was not able to form octamers, forming tetramers instead (data not shown). As discussed above, CΔ111 was also not able to bind ssDNA in high salt. Thus in the case of SrSSB, the C-terminal domain is crucial to both filament formation and ssDNA binding activity in high-salt.

Crystallisation and Structure Determination

Small, prism-shaped crystals of wild-type *S. ruber* SSB were obtained in sitting drops consisting of 1 μl of protein solution (5 mg/ml) containing 20 μM of $d(T)_{75}$ oligonucleotide and 1 μl of reservoir solution (27% w/v PEG 3350, 100 mM Tris-HCl pH 8.0, 0.25M $MgCl_2$, 1 M ammonium sulphate). Soaking experiments were performed by adding $d(T)_8$ oligonucleotide to the drops containing formed crystals, to a final concentration of 0.25 μM.

FIG. 4 shows the crystal structure SrSSB (PDB ID 5ODN) has an octamer as an asymmetric unit build up from a dimer of tetramers. Each OB-fold has bound one short fragment of ssDNA resulting in eight protein and eight ssDNA fragments in the asymmetric unit. The octamerisation interface is shown in FIG. 4A. FIG. 4B shows that the SSB protein forms filaments of tightly packed tetramers (FIG. 3B), even under the high-salt crystallisation conditions used (0.25M $MgCl_2$, 1 M ammonium sulphate).

The invention claimed is:

1. A isolated single-strand DNA binding protein (SSB) which exhibits at least 50% of its maximum ssDNA binding capability in the presence of 500 mM of sodium ions and comprises the amino acid sequence of SEQ ID NO:1 or an amino acid sequence which is at least 75% identical thereto, or a functional fragment thereof, and wherein the amino acid at position 17 and/or 71 has been substituted with an amino acid that lacks a negative charge on its side chain.

2. The SSB of claim 1 comprising the amino acid sequence of SEQ ID NO:2.

3. A composition comprising an isolated SSB which exhibits at least 50% of its maximum ssDNA binding capability in the presence of 500 mM of sodium ions and a buffer and optionally a stabilizing agent, wherein the SSB comprises the amino acid sequence of SEQ ID NO:1 or an amino acid sequence which is at least 75% identical to SEQ ID NO:1, or a functional fragment thereof, and wherein the amino acid at position 17 and/or 71 of the SSB has been substituted with an amino acid that lacks a negative charge on its side chain.

4. A kit comprising the composition of claim 3, and one or more of a polymerase, a washing or other buffer, nucleotides, nucleic acid primers, a ligase, topoisomerase or gyrase.

5. The composition of claim 3, contained within a cartridge which is suitable for use in a sequencing device.

6. A kit comprising the isolated SSB of claim 1, and one or more of a polymerase, a washing or other buffer, nucleotides, nucleic acid primers, a ligase, topoisomerase or gyrase.

7. The SSB of claim 1, contained within a cartridge which is suitable for use in a sequencing device.

8. The SSB of claim 1, wherein the amino acid that lacks a negative charge on its side chain has a positive charge.

9. The SSB of claim 8, wherein the amino acid that lacks a negative charge on its side chain is selected from the group consisting of lysine, histidine, arginine, tyrosine, asparagine and glutamine.

10. The SSB of claim 8, wherein the amino acid that lacks a negative charge on its side chain is lysine or arginine.

11. The SSB of claim 8, wherein the amino acid that lacks a negative charge on its side chain is lysine.

* * * * *

SEQUENCE LISTING

```
<160> NUMBER OF SEQ ID NOS: 11

<210> SEQ ID NO 1
<211> LENGTH: 168
<212> TYPE: PRT
<213> ORGANISM: Salinibacter Ruber

<400> SEQUENCE: 1

Met Ala Arg Gly Val Asn Lys Val Ile Leu Ile Gly Asn Leu Gly Asp
1               5                   10                  15

Asp Pro Glu Leu Arg Tyr Thr Gly Ser Gly Thr Ala Val Cys Asn Met
            20                  25                  30

Ser Leu Ala Thr Asn Glu Thr Tyr Thr Asp Ser Asp Gly Asn Glu Val
        35                  40                  45

Gln Asn Thr Glu Trp His Asp Val Val Ala Trp Gly Arg Leu Gly Glu
    50                  55                  60

Ile Cys Asn Glu Tyr Leu Asp Lys Gly Ser Gln Val Tyr Phe Glu Gly
65                  70                  75                  80

Lys Leu Gln Thr Arg Ser Trp Glu Asp Arg Asp Asn Asn Thr Arg Tyr
                85                  90                  95

Ser Thr Glu Val Lys Ala Gln Glu Met Met Phe Leu Asp Ser Asn Arg
            100                 105                 110

Gln Gly Gly Ala Asp Met Asp Gly Phe Asp Gln Thr Arg Gly Asp Glu
        115                 120                 125

Ser Leu Asp Gln Thr Arg Gln Glu Gln Pro Ala Gly Ser Ser Gly Pro
    130                 135                 140

Gln Pro Gly Gln Gln Ala Ser Ser Gly Gly Glu Asp Glu Asp Thr Phe
145                 150                 155                 160

Glu Pro Asp Asp Asp Leu Pro Phe
                165

<210> SEQ ID NO 2
<211> LENGTH: 168
<212> TYPE: PRT
<213> ORGANISM: Artificial Sequence
<220> FEATURE:
<223> OTHER INFORMATION: D17KD71K SrSSB mutant
```

<400> SEQUENCE: 2

Met Ala Arg Gly Val Asn Lys Val Ile Leu Ile Gly Asn Leu Gly Asp
1               5                   10                  15

Lys Pro Glu Leu Arg Tyr Thr Gly Ser Gly Thr Ala Val Cys Asn Met
            20                  25                  30

Ser Leu Ala Thr Asn Glu Thr Tyr Thr Asp Ser Asp Gly Asn Glu Val
        35                  40                  45

Gln Asn Thr Glu Trp His Asp Val Val Ala Trp Gly Arg Leu Gly Glu
    50                  55                  60

Ile Cys Asn Glu Tyr Leu Lys Lys Gly Ser Gln Val Tyr Phe Glu Gly
65                  70                  75                  80

Lys Leu Gln Thr Arg Ser Trp Glu Asp Arg Asp Asn Asn Thr Arg Tyr
                85                  90                  95

Ser Thr Glu Val Lys Ala Gln Glu Met Met Phe Leu Asp Ser Asn Arg
            100                 105                 110

Gln Gly Gly Ala Asp Met Asp Gly Phe Asp Gln Thr Arg Gly Asp Glu
        115                 120                 125

Ser Leu Asp Gln Thr Arg Gln Glu Gln Pro Ala Gly Ser Ser Gly Pro
130                 135                 140

Gln Pro Gly Gln Gln Ala Ser Ser Gly Gly Glu Asp Glu Thr Phe
145                 150                 155                 160

Glu Pro Asp Asp Asp Leu Pro Phe
                165

<210> SEQ ID NO 3
<211> LENGTH: 507
<212> TYPE: DNA
<213> ORGANISM: Salinibacter ruber

<400> SEQUENCE: 3
atggcacgcg gagtcaacaa ggtcattctc atcggcaacc tcggcgacga tcccgaactg      60
cggtacaccg gcagcgggac ggctgtctgc aacatgtcgc tcgcgaccaa cgaaacctac     120
accgatagcg acggcaatga ggtgcaaaac accgagtggc acgacgtcgt ggcgtggggg     180
cggctcggag agatctgcaa cgagtacctt gacaagggct cccaggtcta cttcgagggc     240
aagctccaaa cccgctcttg ggaggaccgc gacaacaaca cgcgctactc gacggaggtg     300
aaggcccaag agatgatgtt cctcgacagc aatcgccagg gcggggcgga catggacggc     360
ttcgaccaga cccgtgggga cgaatccctg accaaaccc gccaggagca gcccgccggc      420
tcttccggtc cgcagcctgg gcagcaggcg tcctccgggg gcgaggacga ggacacattc     480
gagccggacg atgatcttcc gttctag                                          507

<210> SEQ ID NO 4
<211> LENGTH: 504
<212> TYPE: DNA
<213> ORGANISM: Artificial Sequence
<220> FEATURE:
<223> OTHER INFORMATION: wt SrSSB codon optimized synthetic gene

<400> SEQUENCE: 4
atggcacgtg gtgtgaataa agtgattctg attggtaatc tgggtgatga tccggaactg      60
cgttataccg gtagcggcac cgcagtttgt aatatgagcc tggcaaccaa tgaaacctat     120
accgatagtg atggtaatga agtgcagaat accgaatggc atgatgttgt tgcatggggt     180
cgtctgggtg aaatttgtaa tgaatatctg gataaaggca gccaggtgta ttttgaaggt     240

```
aaactgcaga cccgtagctg ggaagatcgt gataataaca cccgttatag caccgaagtt      300
aaagcccaag aaatgatgtt tctggatagc aatcgtcagg gtggtgcaga tatggatggt      360
tttgatcaga cccgtggtga tgaaagcctg gatcagacac gtcaagaaca gcctgcaggt      420
agcagcggtc cgcagcctgg tcagcaggca agcagcggtg gtgaagatga agatacctttt     480 gaaccggatg atgatctgcc gttt                                              504
```

<210> SEQ ID NO 5
<211> LENGTH: 504
<212> TYPE: DNA
<213> ORGANISM: Artificial Sequence
<220> FEATURE:
<223> OTHER INFORMATION: Nucleotide sequence encoding D17KD71K SrSSB mutant

<400> SEQUENCE: 5

```
atggcacgtg gtgtgaataa agtgattctg attggtaatc tgggtgataa accggaactg      60
cgttataccg gtagcggcac cgcagtttgt aatatgagcc tggcaaccaa tgaaacctat     120
accgatagtg atggtaatga agtgcagaat accgaatggc atgatgttgt tgcatggggt     180
cgtctgggtg aaatttgtaa tgagtacttg aaaaaaggca gccaggtgta ttttgaaggt     240
aaactgcaga cccgtagctg ggaagatcgt gataataaca cccgttatag caccgaagtt     300
aaagcccaag aaatgatgtt tctggatagc aatcgtcagg gtggtgcaga tatggatggt     360
tttgatcaga cccgtggtga tgaaagcctg gatcagacac gtcaagaaca gcctgcaggt     420
agcagcggtc cgcagcctgg tcagcaggca agcagcggtg gtgaagatga agatacctttt    480 gaaccggatg atgatctgcc gttt                                              504
```

<210> SEQ ID NO 6
<211> LENGTH: 36
<212> TYPE: DNA
<213> ORGANISM: Artificial Sequence
<220> FEATURE:
<223> OTHER INFORMATION: Synthetic Primer

<400> SEQUENCE: 6

```
ctttacttcc aggggggccat ggcacgtggt gtgaat                                36
```

<210> SEQ ID NO 7
<211> LENGTH: 36
<212> TYPE: DNA
<213> ORGANISM: Artificial Sequence
<220> FEATURE:
<223> OTHER INFORMATION: Synthetic Primer

<400> SEQUENCE: 7

```
attcacacca cgtgccatgg ccccctggaa gtaaag                                 36
```

<210> SEQ ID NO 8
<211> LENGTH: 36
<212> TYPE: DNA
<213> ORGANISM: Artificial Sequence
<220> FEATURE:
<223> OTHER INFORMATION: Synthetic Primer

<400> SEQUENCE: 8

```
gatgatctgc cgttttaatg aggatccgaa ttcaag                                 36
```

<210> SEQ ID NO 9
<211> LENGTH: 36

```
<212> TYPE: DNA
<213> ORGANISM: Artificial Sequence
<220> FEATURE:
<223> OTHER INFORMATION: Synthetic Primer

<400> SEQUENCE: 9
cttgaattcg gatcctcatt aaaacggcag atcatc                              36

<210> SEQ ID NO 10
<211> LENGTH: 82
<212> TYPE: DNA
<213> ORGANISM: Artificial Sequence
<220> FEATURE:
<223> OTHER INFORMATION: Synthetic Molecular Beacon
<220> FEATURE:
<221> NAME/KEY: modified_base
<222> LOCATION: (7)..(7)
<223> OTHER INFORMATION: dt-4-(4'-dimethylaminophenylazo) benzoic acid
<220> FEATURE:
<221> NAME/KEY: modified_base
<222> LOCATION: (32)..(32)
<223> OTHER INFORMATION: dt-carboxyfluorescein

<400> SEQUENCE: 10
ggcccgtagg aggaaaggac atcttctagc atacgggccg tcaagttcat ggccagtcaa    60
gtcgtcagaa atttcgcacc ac                                             82

<210> SEQ ID NO 11
<211> LENGTH: 150
<212> TYPE: DNA
<213> ORGANISM: Artificial Sequence
<220> FEATURE:
<223> OTHER INFORMATION: Synthetic Biotinylated ssDNA
<220> FEATURE:
<221> NAME/KEY: modified_base
<222> LOCATION: (1)..(1)
<223> OTHER INFORMATION: biotinylated

<400> SEQUENCE: 11
aaagggtatt gacggaccag atgtagcgtg gcagaaaagg gtattgacgg accagatgta    60
gcgtggcaga gactgaaagg gtattgacgg accagatgta gcgtggcaga aaagggtatt   120
gacggaccag atgtagcgtg gcagagactg                                    150
```